United States Patent [19]

Chu

[11] Patent Number: 4,557,764

[45] Date of Patent: Dec. 10, 1985

[54] PROCESS FOR PREPARING MALLEABLE COLLAGEN AND THE PRODUCT THEREOF

[75] Inventor: George Chu, Sunnyvale, Calif.

[73] Assignee: Collagen Corporation, Palo Alto, Calif.

[21] Appl. No.: 648,001

[22] Filed: Sep. 5, 1984

[51] Int. Cl.$^4$ ............................................. C08L 89/06
[52] U.S. Cl. .............................. 106/161; 260/112 B; 260/123.7
[58] Field of Search ..................... 260/112 B, 123.7; 106/161

[56] References Cited

U.S. PATENT DOCUMENTS

| | | | |
|---|---|---|---|
| 3,131,130 | 4/1964 | Oneson | 106/161 |
| 4,295,894 | 10/1981 | Cioca et al. | 106/161 |
| 4,420,339 | 12/1983 | Kato | 106/161 |
| 4,424,208 | 1/1984 | Wallace et al. | 260/112.5 |
| 4,488,911 | 12/1984 | Luck et al. | 106/161 |

Primary Examiner—Theodore Morris
Attorney, Agent, or Firm—Ciotti & Murashige

[57] ABSTRACT

A collagen preparation having unique properties of elasticity and malleability which is associated with a microscopic structure having an intertwining rope-like characteristic, and a process for preparing same are disclosed. The collagen thus formed is the second nucleation product obtained upon incubation of a supernatant from a quick harvested first stage nucleation product.

18 Claims, 2 Drawing Figures

PROCESS FOR PREPARING MALLEABLE COLLAGEN AND THE PRODUCT THEREOF

Technical Field

The present invention relates to preparation of collagen for medical or other associated uses. More specifically, the invention relates to preparation of a collagen composition which is malleable and which has desirable physcial properties.

BACKGROUND ART

Preparations of collagen have found use in a variety of therapeutic and reconstructive contexts in both soft tissue and bone, as well as in the preparation of surgical sponges and associated accessories for medical use.

Collagen is the major protein of the skeletal system, and is found in bone, skin, and cartilage. Native collagen consists in large part of a triple helical structure which appears to be a consequence of repeating triplet sequences composed of glycine linked to two additional amino acids, commonly proline and hydroxyproline, the glycine being in every third position in the chain. In addition, all collagen chains contain regions at each end which do not have the triplet glycine sequence and are thus not helical. These regions are thought to be responsible for the immunogenicity associated with most collagen preparations, and this property can, in large part, be mitigated by removal of these regions to produce "atelopeptide" collagen. The removal can be accomplished by digestion with proteolytic enzymes such as trypsin or pepsin. These non-helical atelopeptide regions are however, required to form the cross-links which are responsible for stability of the fibrillar structure in native collagen, since they contain aldehydes capable of cross-linkage; atelopeptide collagen must be cross-linked artificially if it is desired to obtain this characteristic.

Starting from the native material, derived either from bone or from skin, a variety of approaches to the preparation of pure collagenous materials has been disclosed. For example, Battista, U.S. Pat. No. 3,471,598 and 3,632,361 discloses the preparation of a collagen sponge which is a partial salt formed by preparing a dispersion of the collagen salt in an aqueous medium, casting into a mold and freeze drying. This approach is different from that disclosed in U.S. Pat. No. 3,157,524 which describes a collagen reconstituted by reprecipitation of a solubilized tropocollagen (the basic molecular triple helical unit) from a solution. In addition, commercial preparations commonly known as "Collagenfleece" (U.S. Pat. No. 4,066,083) and Avitene provide relatively pure, contiguous collagen preparations which, however, contain atelopeptides and are often immunogenic.

Other preparations of collagen are available commercially. Prominent among these is Zyderm® collagen implant (ZCI) which is a reconstituted fibrillar suspension of atelopeptide collagen. This preparation is usable in augmenting soft tissue (U.S. Pat. No. 4,424,208) and for cosmetic purposes (when provided as a suspension (U.S. Pat. No. 4,140,537)). The nature of the application to which the collagen preparation is to be put is, of course, instrumental in determining the form of collagen which is most desirable. Certain properties such as, for example, non-immunogenicity are common as desirable to all medical applications. However, other desirable properties vary. For construction of bone replacement material, for example, it would be preferable to have a malleable contiguous mass, whereas for cosmetic "wrinkle-smoothing" applications, an injectable suspension would be preferred. Thus, it is beneficial to provide an arsenal of collagen preparation types whose characteristics offer a spectrum of physical properties.

The present invention adds to the repertoire of available physical properties associated with non-immunogenic collagen preparation.

DISCLOSURE OF THE INVENTION

The present invention provides a malleable, contiguous, elastic form of non-immunogenic collagen which is suitable for a variety of applications. The preparation is characterized on a microscopic scale by interlocking fibrillar ropes having a mean diameter of the order of 170–300 nm, and a microstructure which, within this context, is highly ordered. These physical properties result from a preparation process which employs a secondary nucleation frpm a collagen solution under specified conditions.

Accordingly, in one aspect, the invention concerns a process for preparing a second nucleation form of collagen which process comprises separating a first nucleation product formed by rapid, low temperature mixing of a collagen solution with an insolubilizing buffer, and incubating the remaining collagen in solution to encourage the formation of the desired second nucleation product. The invention, in other aspects, relates to the product of this process, and to collagen preparations having the characteristics associated with it. Included among these characteristics is a microstructure which is predominately formed of interlocking rope-like fibers.

MODES OF CARRYING OUT THE INVENTION

A. Definitions

Figure 1:
FIG. 1 shows a scanning electron micrograph (reflectance) of the collagen preparation under three different ($1000\times$, $6000\times$, and $12,000\times$) magnifications.
Figure 1:
Figure 1:
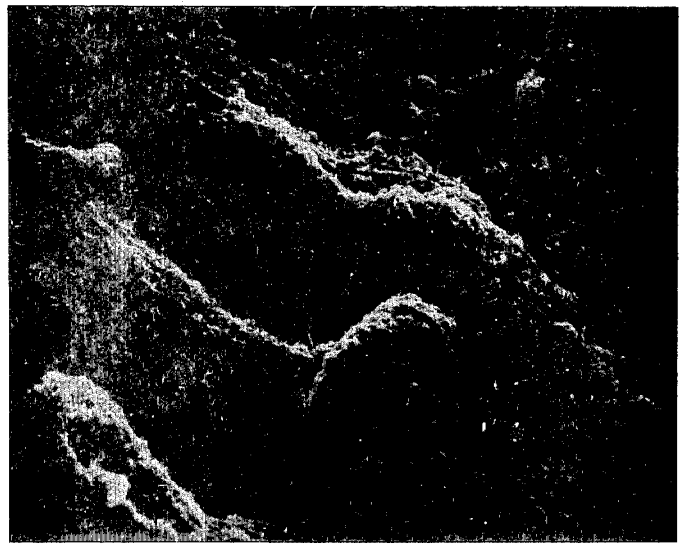

"Second nucleation collagen preparation" refers to a collagen precipitated from solution after a first stage precipitation has already taken place. The collagen preparation of the invention is, indeed, formed by a process which involves pre-precipitation of a "first nucleation" preparation followed by treatment of the resulting supernatant to yield the desired product.

A solution "effective in rendering collagen insoluble" refers to a solution which may be added to a solution containing solubilized collagen which will cause the collagen, in principle, to be unstable in solution, and ultimately to precipitate. The precipitation may not be immediate, due to, for example, formation of a supersaturated solution or other metastable condition. In the process of the present invention, the collagen in solution is typically in a solution of approximately pH 2–3 and the protein is soluble indefinitely in the concentrations used at that pH. However, for example, addition of a solution which converts the pH to approximate neutrality will cause the protein eventually to precipitate. However, the precipitation is a relatively slow process, and depends on the conditions of mixing, temperature, and external forces, such as that exerted by centrifugation, in order for the precipitate actually to appear.

B. Detailed Description

The starting material for the preparation of the collagen of the invention is solubilized collagen in a concentration range of 2 mg/ml to 4 mg/ml. A suitable form of this material is an atelopeptide form of bovine skin collagen, which is commercially available from Collagen Corporation, Palo Alto, Calif., Zygen ® collagen in solution (CIS). This material is a solution containing 3 mg/ml of solubilized collagen at a pH of approximately 2.0. Any solubilized form of collagen can, of course, be used but modifications to the protocols set forth below will undoubtedly be necessary to accomodate to alterations in the starting material. From the standpoint of the physical properties obtained, it may be possible to use collagen which still contains telopeptides; however it is desirable to use an atelopeptide form of solubilized collagen as there would be no particular advantage in using collagen which is known to be immunogenic for medical purposes.

The crux of the process is to form the first nucleation product quickly, under gravitational pressure, and at a temperature gradient in order to provide a supernatant fraction which has the remaining collagen in the correct form for proper formation of the second nucleation batch. To do this, the CIS is rapidly mixed with a solution effective in insolubilizing the collagen—most appropriately a solution which will abruptly raise the pH to approximate neutrality, such as a phosphate buffer of pH above 8. The concentration of the buffer will be compatible with that of the acid components in the CIS so as to result in a final pH of approximately 7 when the appropriate volume is added. It is preferred that the volume ratio of the CIS to that of the added solution be between about 95:5 to 1:1. Each solution is precooled to between 1° C. and 10° C., preferably around 4° C., the two solutions are mixed quickly and the mixture immediately subjected to centrifugation at about $4000 \times g$–$16000 \times g$, preferably around $8000 \times g$–$13000 \times g$ for 1–2 hrs. Thus, during the centrifugation the temperature slowly rises to about room temperature.

As used above, "immediately" refers to a time frame which is in the early lag phase of the fiber formation process. (Collagen fiber formation from solution has been shown to follow a sinusoidal pattern, and it is desired to subject the mixture to the gravitational force before the main thrust of growth phase.) The centrifugation takes place at between about 1° C. to 25° C., preferably around 20° C., and results in a precipitate of between 25% to 60% of the collagen contained in the solution. Optimally, only about 25% of the collagen will precipitate, and the remaining 75% will be available for the second nucleation.

After removal from the centrifuge, the supernatant is gently decanted or otherwise gently removed and incubated at about 15° C.–30° C., preferably around 20° C. from about 4 hrs to about 24 hrs, preferably overnight. During this incubation, the second nucleation preparation forms and is harvested by centrifugation at about 9000 rpm ($13,000 \times g$) for about 10 min. Depending on the amount of collagen precipitated during the first nucleation, about 25–60% will be harvested in this second nucleation step. The remaining supernatant will have a concentration of 0.4–0.7 mg/ml, approximately, of collagen, or about 15% of the total.

Figure 2:
FIG. 2 shows a transmission electron micrograph at $30,000\times$ magnification of the collagen preparation of the invention.

The desired second nucleation product has a set of physical properties useful in applications where malleable or moldable collagen materials are needed. Specifically, precipitate is characterized by a putty-like texture which is cohesive, and which permits molding with only slight resilience and "memory". There are a number of diagnostic characteristics which indicate the presence of these properties. When examined under a scanning electron microscope as shown in FIG. 1, the molecular structure appears to be composed of intertwining rope-like fibers which have diameters in the range of 170–300 nm. This is especially apparent in FIGS. 1b and 1c which show 6,000 and 12,000 fold magnifications respectively. When subjected to transmission electron microscopy the preparation appears as shown in FIG. 2.

These properties appear to result from the manner of handling the first and second nucleations. In a different, but commercially useful process for preparing Zyderm ® collagen implant (ZCI) dispersions, the same starting material can be used. These dispersions, which are prepared at 35 mg/ml (ZCI-I) and 65 mg/ml (ZCI-II) lack the cohesiveness of the present preparation, and do not show the characteristic rope-like structure. While the chemical conditions of precipitation to form ZCI and the preparation of the invention can be identical, the physical conditions are quite different. The ZCI is precipitated at approximately room temperature, by gradual mixing of the insolubilizing buffer and the fibers are permitted to form without centrifugation. The precipitate harvested from the ZCI precipitation yields approximately 85% of the collagen in the precipitate leaving about 15% in the supernatant, approximately the amount found in the supernatant from the second nucleation product of the invention. Thus, ZCI is a first nucleation product and presumably includes additional collagen which would, in the process of the invention, be left to form the desired product. The precipitate in the ZCI dispersion is harvested, homogenized, and formulated to give the commercially available Zyderm ® collagen implant product. It may also be possible to homogenize or otherwise process and formulate the first nucleation product in the process of the invention; thus providing a convenient utility for a major by-product of the invention.

C. Example

The following specific preparation procedure illustrates one embodiment of the invention. It is not intended to limit the scope of conditions under which the process can be carried out.

90 ml of Zygen ® CIS was cooled to 4° C., and quickly mixed in a beaker resting in a 4° C. bath with 10 ml 0.2 M $Na_2HPO_4$ solution which has also been precooled to 4° C. The CIS and phosphate were rapidly thoroughly mixed, and transferred to a centrifuge bottle. The mixture was centrifuged at $10,000 \times g$ for 1.5 hrs at 20° C., and the precipitate thus obtained was separated from the supernatant by gentle decantation. The supernatant was then incubated overnight without stirring at 20° C., and the resulting new precipitate harvested by centrifugation at $13,000 \times g$ for 10 min. The precipitate was harvested by decanting the supernatant.

The precipitated second nucleation product was then subjected to scanning electron microscopy and transmission electron microscopy, giving the results shown in FIGS. 1 and 2 respectively. It was also tested for melting point and showed a higher melting point than ZCI using differential calorimetry. A dispersion of the resulting collagen was capable, at a concentration of 35 mg/ml to be injected with a number 22 needle.

I claim:

1. A process for preparing a second nucleation collagen which comprises:
   (a) mixing at a temperature of about 1°–10° C. a preparation of collagen in solution with a solution effective in rendering the collagen insoluble to give a mixture;
   (b) immediately subjecting the mixture to a force of 8,000–13,000×g to give a precipitate of first nucleation collagen and a supernatant fraction;
   (c) removing the supernatant fraction and incubating said supernatant fraction at about 15°–25° C. for a period effective to form a precipitate of second nucleation collagen; and
   (d) recovering the second nucleation collagen.

2. The process of claim 1 wherein the collagen in solution has a concentration range of 2 mg/ml to 4 mg/ml.

3. The process of claim 1 wherein the collagen in solution is an atelopeptide collagen.

4. The process of claim 3 wherein the collagen in solution is Zygen ® collagen in solution.

5. The process of claim 1 wherein the collagen in solution is in a solution at a pH of approximately 2.

6. The process of claim 1 wherein the mixing temperature is about 4° C.

7. The process of claim 1 wherein the solution effective in rendering the collagen insoluble is a buffer of pH above 7.

8. The process of claim 1 wherein the volume ratio of the CIS to the solution effective in rendering the collagen insoluble is between about 95:5 and 1:1.

9. The process of claim 1 wherein the percentage of total collagen removed in the first nucleation is about 25% to 60%.

10. The process of claim 1 wherein the percentage of total collagen removed in the second nucleation is about 25% to 60%.

11. The process of claim 1 wherein the percentage of total collagen remaining in solution after the second nucleation is about 15%.

12. The process of claim 1 wherein the incubation in (c) is conducted at about 20° C.

13. The process of claim 1 wherein the incubation in (c) is from about 4 hr to 24 hr.

14. The process of claim 1 wherein the second nucleation collagen is recovered by centrifuging at about 13,000×g.

15. Collagen prepared by the process of claim 1.

16. The collagen preparation of claim 1 having a scanning electron micrographic pattern substantially equivalent to that shown in FIG. 1.

17. A collagen preparation comprising rope-like structures which are interlocking, and which have an average diameter of approximately 170–300 nm.

18. The collagen preparation of claim 17 having an appearance in a transmission electron micrograph substantially equivalent to that shown in FIG. 2.

* * * * *